US00PP19003P2

(12) United States Plant Patent
van den Top

(10) Patent No.: US PP19,003 P2
(45) Date of Patent: Jul. 8, 2008

(54) ***HOSTA* PLANT NAMED 'GREAT ESCAPE'**

(50) Latin Name: *Hosta tardiana*
Varietal Denomination: Great Escape

(75) Inventor: Hendrik Jan van den Top, Barneveld (NL)

(73) Assignee: Witteman & Co., Hillegom (NL)

( * ) Notice: Subject to any disclaimer, the term of this patent is extended or adjusted under 35 U.S.C. 154(b) by 0 days.

(21) Appl. No.: 11/725,804

(22) Filed: Mar. 20, 2007

(51) Int. Cl.
*A01H 5/00* (2006.01)

(52) U.S. Cl. ..... Plt./353
(58) Field of Classification Search ..... Plt./353
See application file for complete search history.

*Primary Examiner*—Annette H Para
(74) *Attorney, Agent, or Firm*—C. A. Whealy

(57) ABSTRACT

A new and distinct cultivar of *Hosta* plant named 'Great Escape', characterized by its broadly spreading foliage with upright flower scapes; green and white variegated foliage; violet-colored flowers that are positioned above the foliage on strong scapes; and good garden performance.

2 Drawing Sheets

Botanical designation: *Hosta tardiana.*
Cultivar denomination: 'Great Escape'.

BACKGROUND OF THE INVENTION

The present invention relates to a new and distinct cultivar of *Hosta,* botanically known as *Hosta tardiana* and hereinafter referred to by the name 'Great Escape'.

The new *Hosta* is a naturally-occurring branch mutation of the *Hosta tardiana* cultivar Halcyon, not patented. The new *Hosta* was discovered and selected by the Inventor in a controlled environment in Barneveld, The Netherlands in 2002.

Asexual reproduction of the new *Hosta* by tissue culture in a controlled environment in Barneveld, The Netherlands since 2003, has shown that the unique features of this new *Hosta* are stable and reproduced true to type in successive generations.

SUMMARY OF THE INVENTION

The cultivar Great Escape has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Great Escape'. These characteristics in combination distinguish 'Great Escape' as a new and distinct cultivar of *Hosta:*

1. Broadly spreading foliage with upright flower scapes.
2. Green and white variegated foliage.
3. Violet-colored flowers that are positioned above the foliage on strong scapes.
4. Good garden performance.

Plants of the new *Hosta* differ from plants of the parent, the cultivar Halcyon, primarily in leaf coloration as plants of the cultivar Halcyon have solid green-colored leaves.

Plants of the new *Hosta* can be compared to plants of the cultivar First Frost, not patented. In side-by-side comparisons conducted in Barneveld, The Netherlands, plants of the new *Hosta* and the cultivar First Frost differed in the following characteristics:

1. Young leaves of plants of the new *Hosta* were green and white in color whereas young leaves of plants of the cultivar First Frost were green and yellow in color.
2. The white-colored portion of leaves of plants of the new *Hosta* was larger in area than the white-colored portion of leaves of plants of the cultivar First Frost.

BRIEF DESCRIPTION OF THE PHOTOGRAPHS

The accompanying colored photographs illustrate the overall appearance of the new *Hosta,* showing the colors as true as it is reasonably possible to obtain in colored reproductions of this type. Colors in the photographs may differ slightly from the color values cited in the detailed botanical description which accurately describe the colors of the new *Hosta.*

The photograph on the first sheet comprises a side perspective view of a typical flowering plant of 'Great Escape' grown in an outdoor nursery.

The photograph at the top of the second sheet is a close-up view of typical flowers of 'Great Escape'.

The photograph at the bottom of the second sheet is a close-up view of the upper surface of a typical leaf of 'Great Escape'.

DETAILED BOTANICAL DESCRIPTION

The aforementioned photographs and following observations, measurements and values describe plants grown in containers in Barneveld, The Netherlands, under commercial practice during the late summer in an outdoor nursery with day temperatures ranging from 14° C. to 35° C. and night temperatures ranging from 5° C. to 18° C. Plants had been growing for about one year when the photographs and description were taken. In the following description, color references are made to The Royal Horticultural Society Colour Chart, 2001 Edition, except where general terms of ordinary dictionary significance are used.

Botanical classification: *Hosta tardiana* cultivar Great Escape.

Parentage: Naturally-occurring branch mutation of the *Hosta tardiana* cultivar Halcyon, not patented.

Propagation:

*Type.*—By tissue culture.

*Time to initiate roots.*—About 20 days at 15° C.

*Time to produce a rooted plant.*—About 50 days at 15° C.

*Root description.*—Thick, fleshy; creamy white in color.

*Rooting habit.*—Freely branching.

Plant description:

*Plant form/habit.*—Herbaceous flowering perennial plant. Broadly spreading foliage with upright flower scapes. Flowering stems and leaves basal; moderately vigorous growth habit. Violet-colored flowers are positioned above the foliage on strong scapes.

*Growth rate.*—Moderate to fast; from tissue culture plantlets, about 20 weeks are required to produce fully-grown flowering plants.

*Plant height* (*soil level to top of foliar plane*).—About 9.3 cm.

*Plant height* (*soil level to top of inflorescences*).—About 42.7 cm.

*Plant width* (*spread*).—About 28 cm.

Foliage description:

*Arrangement/form.*—Leaves basal, simple, generally symmetrical and long-persisting.

*Leaf length.*—About 12.6 cm.

*Leaf width.*—About 7.8 cm.

*Shape.*—Broadly ovate to slightly cordate.

*Apex.*—Apiculate.

*Base.*—Broadly ovate to cordate.

*Margin.*—Entire.

*Texture, upper and lower surfaces.*—Smooth, glabrous; slightly rugose.

*Venation pattern.*—Pinnate, arcuate.

*Color.*—Developing leaves, upper surface: Center, 137A; towards the margins, 150D. Developing leaves, lower surface: Center, 137C; towards the margins, between 144A to 144B and 150D. Fully expanded leaves, upper surface: Center, between 137A and 139A; towards the margins, 155A to 155B; venation, center, 137A, and towards the margins, 145B. Fully expanded leaves, lower surface: Center, 137B; towards the margins, 155B; venation, center, 144B, and towards the margins, 145B.

*Petiole length.*—About 7.3 cm.

*Petiole diameter.*—About 5 mm.

*Texture, upper and lower surfaces.*—Smooth, glabrous.

*Color, upper surface.*—137B; towards the margins, 155A to 155B.

*Color, lower surface.*—144B to 144C; towards the margins, 155A to 155B.

Flower description:

*Flower type/habit.*—Numerous single campanulate flowers with fused perianth arranged on terminal racemes; flowers fact outward or slightly downward. Panicles roughly conical in shape. Freely flowering habit with about 25 flowers developing per inflorescence.

*Fragrance.*—Faintly fragrant; sweet.

*Natural flowering season.*—Continuously flowering from summer to early autumn in Barneveld, The Netherlands.

*Postproduction longevity.*—Flowers last about one week on the plant. Flowers not persistent.

*Flower buds.*—Height: About 2.5 cm. Diameter: About 7 mm. Shape: Narrowly obovate. Color: 85B to 85C; longitudinal stripes, 86D.

*Inflorescence height.*—About 13.5 cm.

*Inflorescence diameter.*—About 8 cm.

*Flower diameter.*—About 3 cm.

*Flower depth.*—About 5.2 cm.

*Perianth.*—Arrangement: Three interior tepals arranged in a single whorl surrounded by an outer whorl of three exterior tepals. Tepal length: About 4.5 cm. Tepal width: About 1.2 cm. Tepal shape: Oblanceolate. Tepal apex: Acute. Tepal margin: Entire. Tepal texture, upper and lower surfaces: Smooth, glabrous. Tepal color: Developing petals, upper surface: 85D; longitudinal stripes, 85A to 85B. Developing petals, lower surface: 85C to 85D. Fully expanded petals, upper surface: 85D; longitudinal stripes, 85A to 85B. With development, color becoming closer to 91D. Fully expanded petals, lower surface: 85C to 85D; longitudinal stripes, 85A to 85B.

*Flower bracts.*—Quantity: One per flower at the base of the pedicel. Length: About 1.5 cm. Width: About 5 mm. Shape: Ovate. Apex: Acute. Base: Cuneate. Margin: Entire. Texture, upper and lower surfaces: Smooth, glabrous. Color, upper and lower surfaces: N77C; towards the apex, 146B to 146C.

*Peduncles* (*scapes*).—Length: About 41.2 cm. Diameter: About 4 mm. Angle: Erect. Strength: Strong. Texture: Smooth, glabrous. Color: 144A.

*Pedicels.*—Length: About 6 mm. Diameter: About 1.5 mm. Angle: About 50° from vertical. Strength: Strong. Texture: Smooth, glabrous. Color: 85D.

*Reproductive organs.*—Stamens: Quantity per flower: Typically six; anthers dorsifixed. Filament length: About 4.5 cm. Filament color: 145C to 145D. Anther shape: Narrowly oblong. Anther length: About 4 mm. Anther color: 198A to 198B. Pollen amount: Moderate. Pollen color: 17A to 17B. Pistils: Quantity per flower: One. Pistil length: About 4.9 cm. Stigma shape: Crested. Stigma color: 155C. Style length: About 4.9 cm. Style color: 155A; towards the base, 145D. Ovary color: 145A.

*Seed/fruit.*—Seed and fruit development have not been observed.

Disease/pest resistance: Plants of the new *Hosta* have not been noted to be resistant to pathogens and pests common to *Hosta*.

Garden performance: Plants of the new *Hosta* have been observed to have good garden performance and tolerate rain, wind and high temperatures of about 32° C. Plants of the new *Hosta* have been observed to be hardy to USDA Zone 5.

It is claimed:

1. A new and distinct *Hosta* plant named 'Great Escape' as illustrated and described.

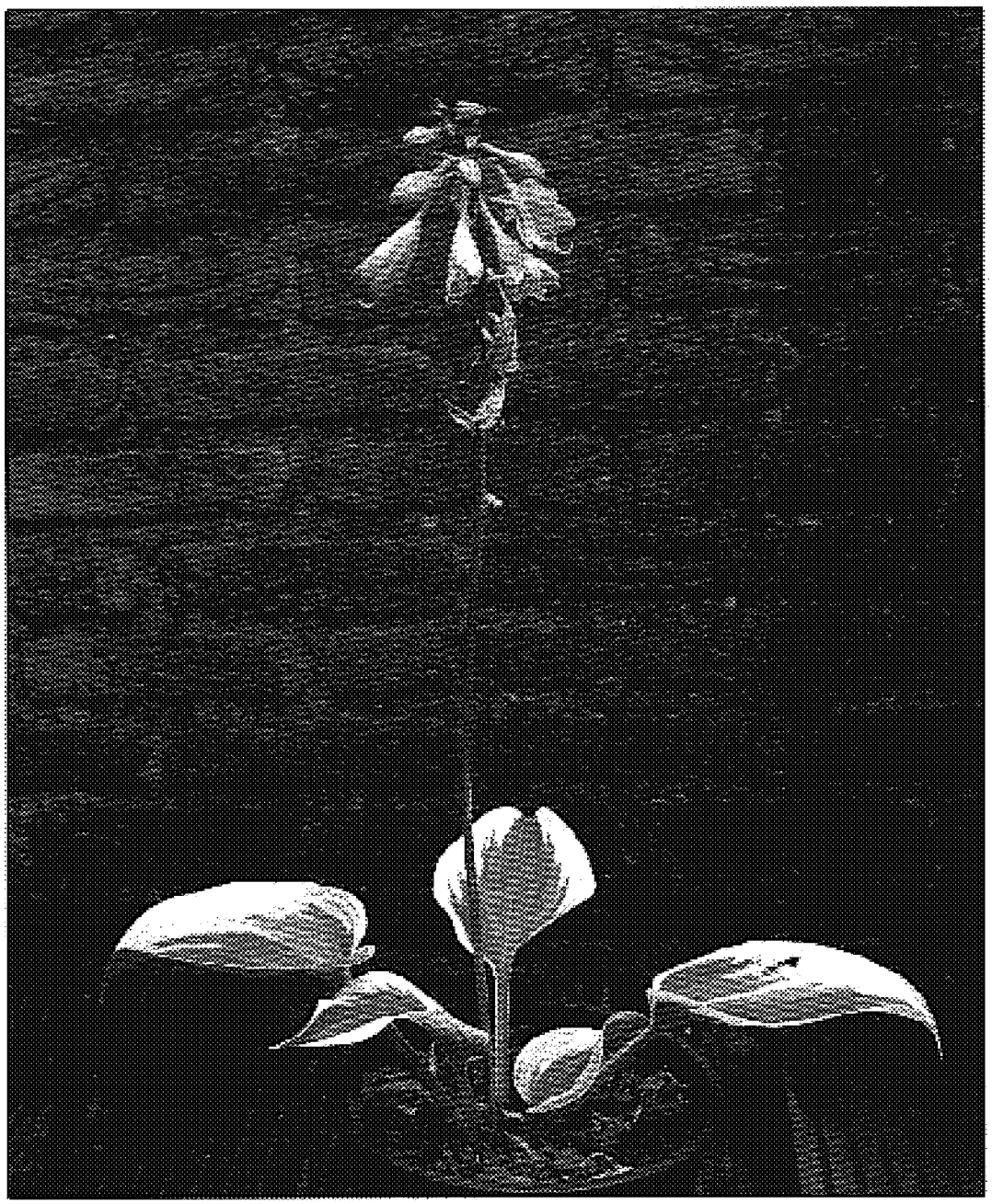

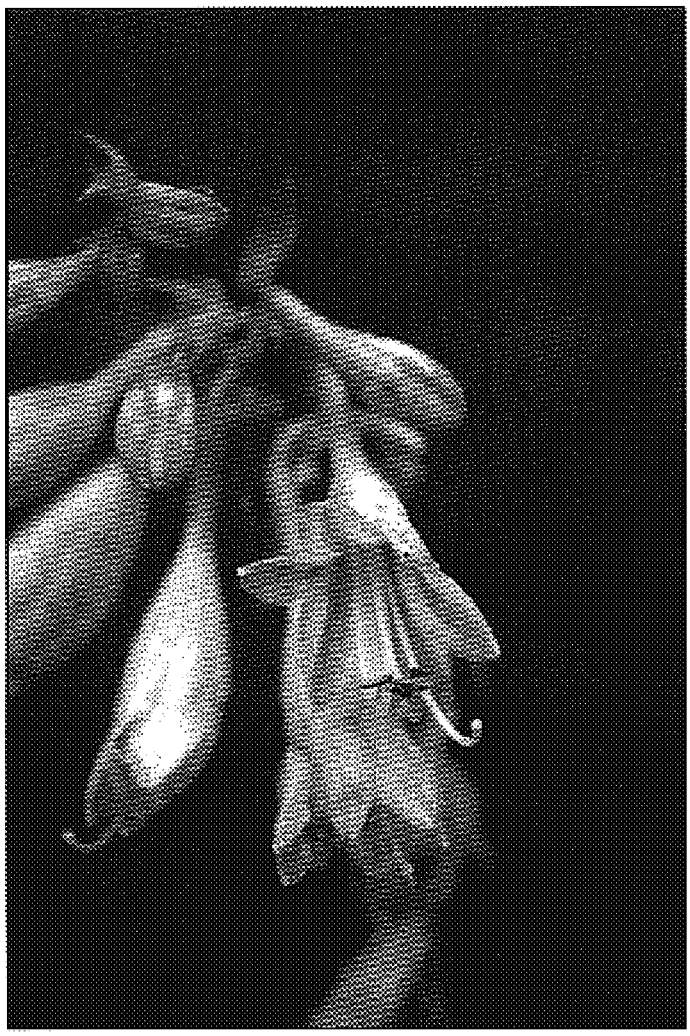
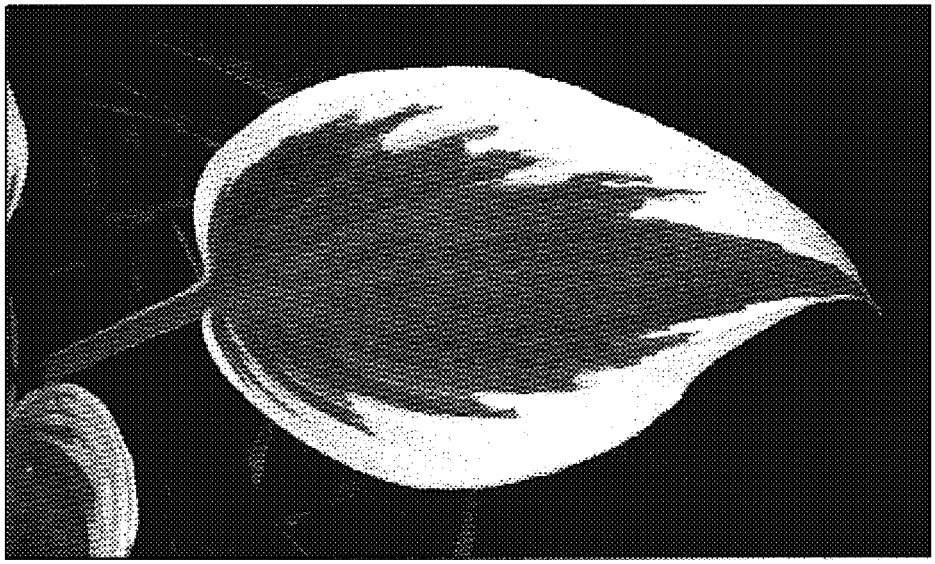

* * * * *